US006673621B1

(12) United States Patent
Mitchell

(10) Patent No.: US 6,673,621 B1
(45) Date of Patent: Jan. 6, 2004

(54) SAMPLE COLLECTION DEVICES AND METHODS USING MARKERS AND THE USE OF SUCH MARKERS AS CONTROLS IN SAMPLE VALIDATION, LABORATORY EVALUATION AND/OR ACCREDITATION

(75) Inventor: Lloyd G. Mitchell, Durham, NC (US)

(73) Assignee: Intronn LLC, Durham, NC (US)

( * ) Notice: Subject to any disclaimer, the term of this patent is extended or adjusted under 35 U.S.C. 154(b) by 0 days.

(21) Appl. No.: 09/147,698

(22) PCT Filed: Oct. 3, 1997

(86) PCT No.: PCT/US97/17313
§ 371 (c)(1),
(2), (4) Date: Jun. 9, 1999

(87) PCT Pub. No.: WO98/14275
PCT Pub. Date: Apr. 9, 1998

Related U.S. Application Data
(60) Provisional application No. 60/027,647, filed on Oct. 4, 1996.

(51) Int. Cl.[7] ............................ G01N 37/00; G01N 21/91
(52) U.S. Cl. ............................. 436/56; 435/6; 422/102; 436/94
(58) Field of Search ........................ 436/56, 94; 435/6; 422/102

(56) References Cited

U.S. PATENT DOCUMENTS

| | | | | |
|---|---|---|---|---|
| 4,223,004 A | * | 9/1980 | Hsia et al. ..................... 424/9 |
| 4,953,562 A | * | 9/1990 | Rosen et al. .................. 128/771 |
| 5,179,027 A | * | 1/1993 | Fisher .......................... 436/56 |
| 5,215,102 A | * | 6/1993 | Guirguis ....................... 128/771 |
| 5,223,221 A | * | 6/1993 | Copelan ....................... 422/61 |
| 5,310,653 A | * | 5/1994 | Hanausek-Walaszek et al. . 435/7.23 |
| 5,482,834 A | * | 1/1996 | Gillespie ...................... 435/6 |
| 5,587,294 A | * | 12/1996 | Tamarkin et al. .......... 435/7.93 |
| 5,776,737 A | * | 7/1998 | Dunn .......................... 435/91.1 |

* cited by examiner

*Primary Examiner*—Jill Warden
*Assistant Examiner*—Monique T. Cole
(74) *Attorney, Agent, or Firm*—Arent Fox Kintner Plotkin & Kahn, PLLC

(57) ABSTRACT

The invention is directed to a device suitable for marking a collected sample, comprising collecting means for collecting the sample and at least one detectable marker which is associated with at least a portion of the collecting means, wherein the at least one detectable marker is contractable with the sample upon collection of the sample to mark the collected sample upon contact of the sample with the at least a portion of the collecting means having the at least one detectable marker associated therewith, and wherein the at least one detectable marker is other than a component which is present in the sample before collection and is inert to any component present in the sample before collection. Kits containing the device, methods for marking samples using the device, methods for determining the integrity of a marked sample, and use of the markers for the testing of laboratories and/or laboratory personnel for certification, proficiency testing or accreditation purposes are also provided.

22 Claims, 2 Drawing Sheets

SAMPLE COLLECTION DEVICES AND METHODS USING MARKERS AND THE USE OF SUCH MARKERS AS CONTROLS IN SAMPLE VALIDATION, LABORATORY EVALUATION AND/OR ACCREDITATION

This application claims the benefit of provisional application Ser. No. 60/027,647 filed Oct. 4, 1996.

BACKGROUND

The present invention relates to a device and method for collecting blood and other body fluids, such as urine, saliva, cerebral spinal fluid, etc., and tissues from individuals and/or animals in forensic, clinical, paternity, veterinary or other types of sample testing to uniquely mark the specimen to be studied, so that any contamination and/or tampering will be readily detectable. This method may also be applied to the marking of other samples, such as those derived from plants, animals, or non-biologic origins. The markers of the present invention may also be used as controls in evaluating laboratory procedures, such as sample handling, and/or for the testing of forensic, clinical, paternity, veterinary or other laboratories or personnel for certification, proficiency testing, or accreditation purposes.

Samples are collected for analysis by many methods for many different purposes, including to establish identity by DNA analysis. Misidentification and cross-contamination of samples are two problems that must be eliminated to ensure the validity of any test results. The handling of samples for forensic identification has caused problems for investigators and laboratories analyzing crime scene evidence and suspect samples. Defense attorneys are frequently successful in acquitting their clients if they can impugn the forensic evidence on the basis of inadvertent or deliberate contamination of the crime scene evidence with material (blood or DNA) obtained from a suspect (i.e., the defendant). The case of O. J. Simpson vs. State of California is a notorious example where the integrity of the DNA evidence was questioned.

There are approximately 3.3 billion DNA base pairs in the human genome, and many regions vary between individuals, thus making the identification of a unique individual possible. DNA regions are chosen for forensic analysis on the basis of specificity to humans and degree of polymorphism, that is the polymorphic regions are likely to differ between randomly chosen individuals.

There are many DNA sequences from other species which are not present in human DNA which should not interfere with the analysis of human genetic polymorphism. These include bacterial genes (such as neomycin and other antibiotic resistance genes), phage, yeast, non-primate animal and plant genes. The sequence of many of these genes are known and they are relatively easy to produce and test for lack of cross-reactivity in current forensic or other tests. Additionally, completely artificial DNA sequences can be made which have no human analogs. These sequences can be used to mark samples at the time of collection, so that any subsequent cross-contamination can be determined.

Recently, there has been mounting pressure for laboratories that handle body fluid and tissue samples to submit to certification, proficiency testing and/or accreditation, to ensure that a particular laboratory is professionally run and meets with certain national standards. Markers such as those illustrated above, and/or non-nucleic acid markers such as proteins or peptides, chemicals or elements, can be used as controls in evaluating laboratory procedures, such as sample handling, for purposes of such certification, proficiency testing and/or accreditation.

There exist numerous tamper-resistant devices for collecting samples in the art. For example, U.S. Pat. No. 4,873,193 is directed to a method and apparatus for the collection and preservation of fluid biological evidence. The apparatus comprises a specimen vial and lid, with the lid having an adhesive coated disk inserted therein. The lid is initially inverted on the rim of the specimen vial and is encased in a tamper-evident plastic wrapper. The specimen vial and lid, encased in the tamper evident wrapper, are sealed within an outer container with a second tamper evident plastic wrapper. The container exists in a tamper-evidencing state prior to the product being placed therein. This first tamper-evidencing seal is broken, the item of evidence is placed therein, and the container is thereafter resealed once the item has been placed in the container. A new tamper-evident seal is thus created. There is no disclosure in the '193 patent of adding markers to the specimen vial to prevent tampering.

There also exist numerous methods and kits for tagging substances. For example, U.S. Pat. Nos. 4,953,562, 5,039, 616 and 5,179,027 are all directed to tagging for the purposes of preventing the introduction of false specimens in urinalysis. These patents are directed to identifying the source of urine samples collected for biochemical analysis where there is a potential for laboratory error or deceptive substitution of one urine specimen for another. In these methods of urine specimen identification, the individual whose urine is to be tested consumes one or more formulations containing one or more harmless identifying substances that can be rapidly absorbed by the body and will quickly appear in the urine. The collected urine is later analyzed for the presence of these substances, thereby determining the source of the specimen and detecting any error or deceptive substitution thereof. There is no disclosure in these patents of adding markers to the collection device before the urine sample is added thereto. Instead, all of the markers are first consumed by the individual who is to provide the sample. The urine sample is thus "tagged" before it is collected.

U.S. Pat. No. 4,441,943 is directed to a method of tagging a substance to allow for the subsequent identification thereof by incorporating a polypeptide into the substance. Example substances to be tagged include explosive compositions or oil. The '943 patent discloses incorporating tags into the substance to be tagged and thereafter releasing the tagged substances into their normal environments of use. After an accident or illegal activity involving the tagged substances, the tagged substances are collected, and the tags are examined for information on their origination. There is no disclosure of a sample collection device having markers associated with the device.

U.S. Pat. No. 5,451,505 is directed to methods for tagging and tracing materials using nucleic acids as taggants. More particularly, the invention provides for a method of monitoring the presence of a substance by tagging the substance with a nucleic acid, collecting the substance and detecting the nucleic acid. The materials or substances contemplated for tagging include air pollutants, oils, aromatic compounds, explosive compositions, foodstuffs, medicaments, inks, paper goods and paint products. There is no disclosure of a sample collection device having markers associated therewith.

BRIEF SUMMARY OF THE INVENTION

The present invention provides a sample collection device and method which minimizes the risk of undetected cross-contamination due to error or fraud. A method of and a device for marking a sample from a given individual, animal, plant or non-biologic substance from the moment of sample collection is provided (i.e., identifying that a particular sample came from a given individual, animal, plant or non-biologic substance), as well as a method for determining the integrity of a sample (i.e., the presence or absence of extraneous markers, which would signal contamination, or the determination of sample deterioration). The present device and method provide a means for determining whether or not cross-contamination has occurred at any subsequent point in the handling of sample materials.

Specifically, the present invention includes a device suitable for marking a collected sample, comprising:

collecting means for collecting the sample; and at least one detectable marker which is associated with at least a portion of the collecting means, wherein the at least one detectable marker is contactable with the sample upon collection of the sample to mark the collected sample upon contact of the sample with the at least a portion of the collecting means having the at least one detectable marker associated therewith, and wherein the at least one detectable marker is other than a component which is present in the sample before collection and is inert to any component present in the sample before collection.

Also included in the invention is a kit suitable for marking a body fluid evidence sample, comprising the device as described above, means for identifying at least one of the identity and the amount of the at least one detectable marker and tamper-evident sealing means for tamper-evident sealing of the collecting means and the at least one detectable marker.

The invention further includes a method for marking a sample, comprising collecting the sample using a collection device having at least one detectable marker which is associated with at least a portion of the collecting device, wherein the at least one detectable marker is other than a component which is present in the sample before collection and is inert to any component present in the sample before collection, and causing the sample to contact the at least one detectable marker to pass at least a portion of the at least one detectable marker into the sample to mark the sample.

The invention also includes a method for determining the integrity of a marked sample, comprising:

(a) providing a sample which is marked as recited above;

(b) thereafter detecting at least one of an identity and an amount of the at least one detectable marker to provide a result; and (c) comparing the result from step (b) with known information as to at least one of the identity and the amount of the at least one detectable marker to determine the integrity of the marked sample.

The invention further includes a method for using at least one detectable marker to determine the integrity of a marked sample in a certification or accreditation procedure, the method comprising:

(a) providing a sample comprising a test material and at least one detectable marker to a test laboratory for testing the test material, wherein the at least one detectable marker is present in the sample in at least one of an identity and an amount which is unknown to the test laboratory;

(b) obtaining at least a portion of the sample from step (a) after the test material has been tested by the test laboratory;

(c) thereafter detecting at least one of the identity and the amount of the at least one detectable marker to provide a result; and (d) comparing the result from step (c) with known information as to at least one of the identity and the amount of the at least one detectable marker to determine the integrity of the marked sample.

The use of at least one detectable marker in laboratory testing to ensure sample integrity and as a control in evaluating laboratory procedures is also included, along with the use of at least one detectable marker for the testing of laboratories and/or laboratory personnel for certification, proficiency testing or accreditation purposes.

The invention further includes the use of at least one detectable marker in the manufacture of a device suitable for marking a sample, wherein the at least one detectable marker is other than a component which is already present in the sample and is inert to any component already present in the sample.

Figure 1:
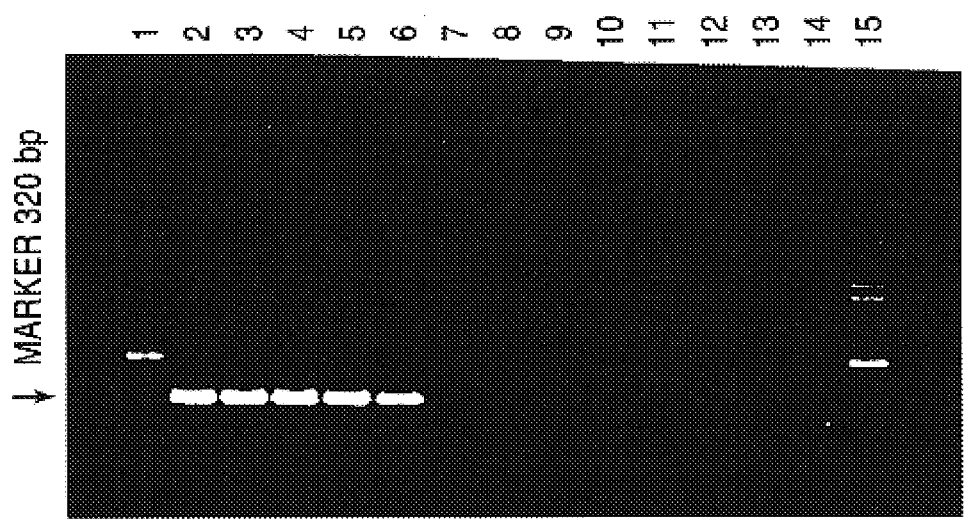
FIG. 1 is a test of marker DNA for co-migration with DNA extracted from whole blood using Chelex extraction. The Chelex DNA extraction/purification procedure (Bio-Rad Laboratories) may reduce marker DNA concentration by a factor of $10^5$ from the initial amount added to a whole blood sample. A 302 bp fragment of the marker was PCR amplified from 13 samples (including 3 negative controls) after the Chelex extraction, and the resulting products were electrophoresed on a 1% agarose gel, stained with ethidium bromide and photographed.

Lanes 1 and 15 contained a 100 bp ladder; lane 2 had 100 ng of marker added to 10 μl blood prior to extraction; lane 3 had 10 ng of marker; lane 4 had 1 ng of marker; lane 5 had 100 pg of marker; lane 6 had 10 pg of marker; lane 7 had 1 pg of marker; and lanes 8 through 11 had 100 fg, 10 fg, 1 fg and 0.1 fg of marker, respectively. Lanes 12–14 were negative controls containing processed blood, but no marker.

Final concentrations of marker detected range from 1 pg (lane 2) to 10 ag (attogram), which is the equivalent to about 10 molecules.

Figure 2:
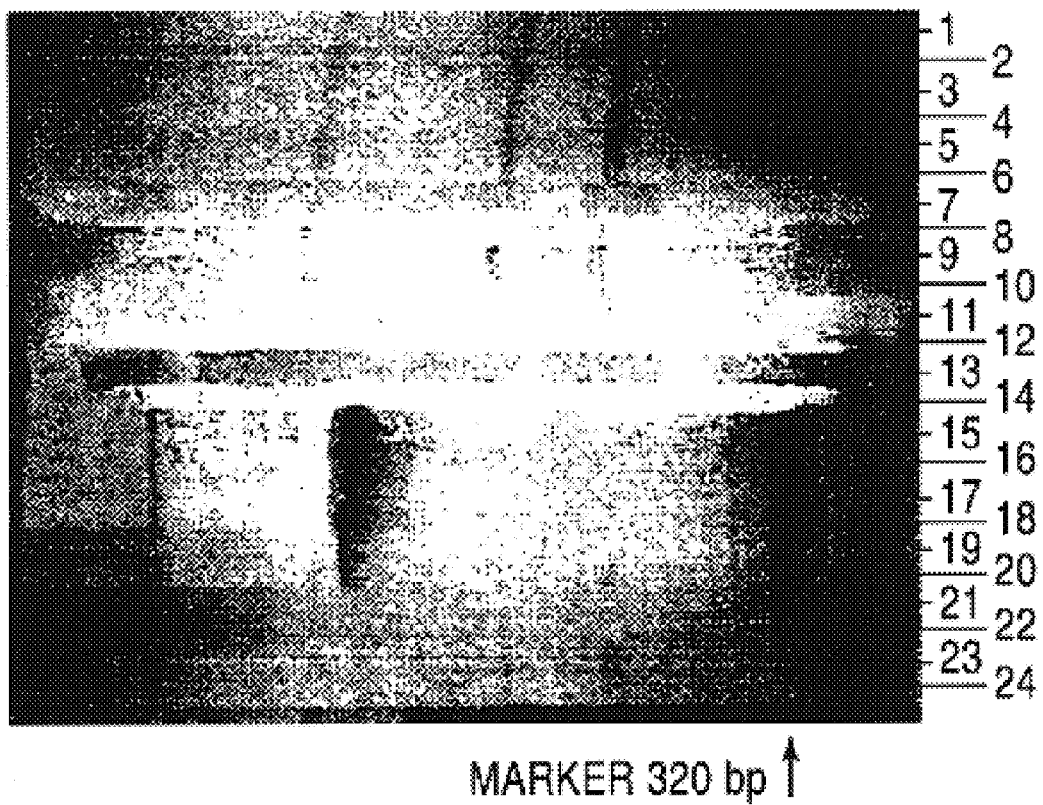

FIG. 2 is a silver stained polyacrylamide gel of marker dilutions spiked into a mixture of three commonly used forensic STR's (Short Tandem Repeats) for vWF, THO1 and TPOX (lanes 1–13), and the detection of the marker from an aliquot of each PCR amplified STR reaction (lanes 14–24).

Three primer combination PCR was performed using primers to amplify STR fragments for vWF, THO1 and TPOX (Promega Inc.) using K562 human DNA template. Lanes 2–6 and 8–11 are identical, except that they contain different amount of marker DNA (produced from a fragment of *Corynebacterium diphtheriae* DNA) ranging from 10 ng (Lane 1) to 0.1 fg (Lane 10). No interference with the STR is noted.

| Lane | Marker concentration |
| --- | --- |
| 1 | 10 ng |
| 2 | 1 ng |
| 3 | 100 pg |
| 4 | 10 pg |
| 5 | 1 pg |
| 6 | 100 fg |
| 8 | 10 fg |

-continued

| Lane | Marker concentration |
| --- | --- |
| 9 | 1 fg |
| 10 | 100 ag |
| 11 | 0 (Negative Control) |
| 12 | 100 ng (contains no human DNA) |

Lanes 7 & 13 contained mixed STR electrophoretic gel size markers for vWF, THO1 and TPOX (Promega Inc.).

Two microliters of each STR PCR product from above ($4 \times 10^{-2}$ dilution) was PCR amplified to detect the presence of marker using primers which amplified a 302 bp segment of the *Corynebacterium diphtheriae* genome. Detection of the marker was achieved at approximately 40 ag (attograms, lane 22) of marker, which is in the range of 30 to 100 marker molecules.

| Lane | Reamplified from sample in lane | Marker concentration |
| --- | --- | --- |
| 14 | — | 0 (Neg. cont'l, cont. human K562 DNA) |
| 15 | 1 | 400 pg |
| 16 | 2 | 40 pg |
| 17 | 3 | 4 pg |
| 18 | 4 | 400 fg |
| 19 | 5 | 40 fg |
| 20 | 6 | 4 fg |
| 21 | 8 | 400 ag |
| 22 | 9 | 40 ag |
| 23 | 10 | 4 ag |
| 24 | — | 0 (Neg. cont'l, no DNA except primers) |

This gel demonstrates that the non-human marker does not interfere with a commonly performed forensic test. There is no difference in the results from samples containing the marker versus ones without. Additionally, the marker can be detected with a high degree of sensitivity in a sample that has been previously tested for other purposes.

DETAILED DESCRIPTION OF THE INVENTION

The present invention includes methods and devices for marking a collected sample, and the use of such markers in forensic, clinical, paternity or veterinary testing to ensure sample integrity, or as a control in evaluating laboratory procedures, or for certification, proficiency testing or accreditation purposes. The sample can be an animal sample, a human sample, a plant sample, or a non-biologic sample. By "ensuring sample integrity" the inventor means not only determining whether any contamination has occurred, but it can also mean determining whether any degradation or deterioration of the sample has taken place. The present invention preferentially includes the steps of producing nucleic acids (such as DNA, RNA, peptide nucleic acids or hybrids thereof) and/or other markers (such as proteins, peptides, chemicals and/or elements) which do not interfere with sample analysis (i.e., are inert to, that is, substantially unreactive with, components already present in the sample) and adding one or more of these markers to individually registered sample collection or laboratory control devices. A combination of marker nucleic acids and/or other markers would be present in all samples claimed to have been derived from the marked sample. If the proper combination of markers cannot be detected in the marked samples, test results claimed to have come from the marked sample would be suspect. If the combination of markers present in the marked sample was detected in any non-marked samples (such as crime scene evidence in forensic analysis), this would strongly indicate contamination of the non-marked samples. The use of marked samples marked using the method and device of the present invention for forensic purposes would therefore remove any doubt in the mind of trial juries as to the integrity of the sample.

The markers of the present invention can be used as controls in evaluating laboratory procedures. The markers can be added to a laboratory control device in a concentration which is known to the laboratory to provide an internal standard against which laboratory equipment and personnel can be tested. A laboratory can use the markers of the present invention, provided in such a manner as described above, for quality control, sample validation, determination of sample contamination or mix-up, tests for sample handling or proficiency testing. The presence of the markers indicates whether the laboratory is operating in an acceptable manner.

The markers of the present invention can also be used to determine the integrity of a marked sample in a certification or accreditation procedure. The method first includes a reference laboratory providing a sample comprising a test material (such as a DNA to be tested) and at least one detectable marker to a test laboratory for testing the test material, where the at least one detectable marker is present in the sample in an identity and/or an amount which is unknown to the test laboratory. The test laboratory then conducts its tests on the test material (such as testing for polymorphic regions). Thereafter, at least a portion of the sample is obtained by the reference laboratory, after the test material has been tested by the test laboratory. The reference laboratory then determines the integrity of the sample by detecting the identity and/or the amount of the at least one detectable marker, and comparing the results with known information as to the identity and/or the amount of the detectable marker. The results would be evaluated by the reference laboratory for compliance with national standards. If the laboratory to be tested was in compliance with the standards, the laboratory would receive certification or accreditation. The amount and types of markers would be known only to an outside or reference laboratory which has been previously certified or approved to perform reference work in a competent and objective manner.

In addition to nucleic acid markers, the present invention also contemplates the use of non-nucleic acid markers. These non-nucleic acid markers may be included instead of or in conjunction with nucleic acid markers. The non-nucleic acid markers may be any of a wide range of materials, as long as they aid to establish the identity of a sample and can be used to determine the presence or absence of the marked sample from other samples which may be processed by the same laboratory personnel or in the same physical location.

The collection or laboratory control device of the present invention is not limited to a particular physical structure. The collection or control device of the present invention may be any device which is capable of containing a sample. Preferred devices include a tube (preferably under vacuum) or a membrane collection system, such as filter paper or other blood collection matrix (such as FTA® paper from Fitzco or Scleicher & Schuell's Isocode® matrix). The device chosen preferentially contains means for identifying the identity and/or the amount of the detectable marker in code, such as a unique serial number, bar code or other known identifier used to identify the device, which is correlated to the one or more detectable markers contained therein. No matter what physical form the collection or control device comprises, each device is manufactured with one or more nucleic acid and/or non-nucleic acid markers. The markers may each be added individually into the device, or may be combined prior to being added to the device. If the collection or control device is a tube under vacuum, the markers may be added after the tube is evacuated and sealed. For a membrane collection system, the markers can be applied to the membrane in a manufacturing facility, or sample blood may be collected in a syringe or vacuum tube which contains a set of markers, and then applied to the membrane collection system. Additionally, markers which are non-toxic may be used to coat the inside of the collection hypodermic needle and any intermediate sample handling devices, such as tubing or syringes.

The markers included in the present invention may be human or non-human nucleic acid sequences or other non-nucleic markers which are easily detectable with specific probes, by PCR amplification, or by other methods obvious to those of skill in the art, and are present at sufficient concentrations so that they continue to be detectable after the marked sample is processed by the methods routinely used in forensic, clinical, paternity or veterinary analysis. The organisms from which the nucleic acid markers are derived should not normally be present in the environment from where the sample is collected, such as crime scenes or other locations which can render the sample suspect. Examples of acceptable nucleic acid markers include nucleic acid sequences from organisms native to deep sea, hot springs, mountain, or arctic environments. This could encompass sequences from organisms such as penguins, condors, deep sea vent tube worms, and even extinct animals such as the mammoth, passenger pigeon and quagga. Additionally, the nucleic acid or non-nucleic markers should not interfere with any test procedure to be performed upon the marked sample, examples of which would be cross-reacting with hybridization probes or amplification primers, or altering the electrophoretic mobility of DNA derived from the marked sample, compared to unmarked DNA from the same source.

Markers used in accordance with the invention in forensic laboratories should be tested in commonly used forensic procedures to determine that they do not interfere with the forensic test results. No matter which type of laboratory is conducting tests on the sample, the nucleic acid markers can be detected using standard techniques described in the literature, for example, in *Molecular Cloning: A Laboratory Manual,* 2nd Edition, Maniatis et al., eds., Cold Spring Harbor, N.Y. (1989), which techniques are hereby incorporated by reference. Typically, the presence of one or more nucleic acid markers in an alleged marked sample can be proven by detection of the appropriate bands using probes or primers specific for those markers, thereby establishing that the marked sample was obtained from the marked collection device. If any marker was missing, or if additional markers were identified in the marked sample, this would indicate possible misidentification of the sample or tampering. Non-nucleic acid markers also may be included in the present invention, such as peptides, proteins, fluorescent compounds, chemicals or elements with isotopically different mass units, stains and dyes, which would be detected by suitable methods known in the art, such as fluorescence of a known compound or a detection of marker chemicals, proteins or non-radioactive isotopes by methods such as mass spectroscopy, HPLC, immunoreactivity, capillary electrophoresis or other means known to those skilled in the art.

Chemical libraries or families of compounds of various lengths and composition can also be produced and used as markers in accordance with the present invention. Such chemical libraries can include combinations of amino acids, amino alcohols, functionalized sulfonyl chlorides, isocyanates, carboxylic acids, chloroformates (see Baldwin et al, *J. Am. Chem. Soc.* 117, pp. 5588–89 (1995), hereby incorporated by reference) and secondary amines (see *Ni et al, J Med. Chem.* 39, pp. 1601–08 (1996), hereby incorporated by reference). Compounds such as those described above may be alicyclic, aliphatic, aromatic, heterocyclic, may contain fluorocarbons, chlorocarbons (such as halogenated benzenes, see Nestler et al, *J. Org. Chem.* 59, pp. 4723–24 (1994), hereby incorporated by reference) or other substitutive groups which produce a distinct detectable profile. In addition, microchips (beads) which are encoded with a radiofrequency transponder can also be used (see Moran et al, *J. Am. Chem. Soc.* 117, 10787–88 (1995), hereby incorporated by reference). Marker chemicals used should be readily detectable by sensitive methods such as electron capture gas chromatography, mass spectrometry (including electrospray ionization and matrix assisted laser desorption MS), liquid chromatography, thin layer chromatography or UV/visible light spectroscopy.

The collection device will preferably have additional security features to protect against tampering. In a preferred embodiment, a collection device will have a tamper-evident security seal over the device and would be sealed within a tamper-resistant pouch with the serial number of the device imprinted on the pouch and the device itself. When sample collection is necessary, the sample donor can be given a photograph of an intact collection device and the intact external seals before sample collection is undertaken, and would be asked to sign or initial that the security seals were intact prior to the sample collection. A second witness, in addition to the collection agent (i.e., phlebotomist) may also be required. According to the present invention, the sample will be instantly marked upon delivery of the sample into the collection device, as the one or more makers are present within the collection device. The security seals will insure that the markers are not removed from the collection device by anyone intent on tampering or defeating this system.

The identity and/or amount of the markers used within any particular collection or control device will be withheld from the end user, except in well defined circumstances. For example, markers can be supplied in known identities and amounts in a control device for detection by a laboratory as part of an internal control procedure. For sample collection devices containing marked samples, or for control devices used for certification and/or accreditation, the presence or absence of unknown markers may be determined by an outside laboratory having knowledge of the identity and amount of the markers used within the collection device. The outside laboratory may be certified or approved and should be competent to perform this work in a competent and objective manner. This should serve to protect the integrity of the one or more markers from intentional, fraudulent manipulation.

All non-marked samples (e.g., crime scene evidence in forensic analysis) can be tested by DNA amplification (if nucleic acid markers are used) with the appropriate primers for the marker nucleic acids. Lack of amplification of marker nucleic acid sequences would strongly suggest that cross-contamination had not occurred between the marked and unmarked samples. A positive marker amplification from material collected at the crime scene would strongly suggest that there was contamination of the unmarked sample by the marked sample, and that any such contaminated evidence should be discounted. To evaluate the possibility that an organism(s) which was used as a source of nucleic acid marker sequence was truly present at a crime scene and that marker nucleic acid sequences from the organism were found due to the organism's presence at the crime scene, amplification primers or other indicators (such as probes) could be generated for non-marker regions of the organism's genome which were not added to the collection device. By the use of combinations of markers derived from diverse organisms, the probability of crime scene contamination with DNA from all of the organisms used to produce marker sequences would be exceedingly small.

Some of the benefits of the present invention are as follows:

- The technology provides a means of testing for contamination between samples such as evidentiary samples, which can be used to test whether laboratories are having sample handling problems. The markers can be used in a certification process for laboratories and individual technicians.
- The individual's sample is immediately marked at the time of collection. This feature can be used to resolve any questions of sample validity or integrity. A unique set of markers can be used to identify each sample, if desired.
- In forensic analysis, the conclusions derived from crime scene evidentiary samples can be validated by absence of the markers contained in a sample collected from the suspect.
- In the event of label destruction on the collection device, a patient's sample can be traced back to the patient by analyzing the markers present in the sample, and correlating the identity and/or amount of markers to the collection device. A separate record will indicate that the patient's sample was assigned to that specific collection device, thus authenticating the identity of the sample.
- The amount and/or identity of the markers used is unknown to the personnel processing the sample, except when used as an internal control.
- Markers used can be chemical, protein or nucleic acid in origin, or a combination of these. This provides further assurances that tampering can be determined.

EXAMPLES

Example 1

Collection of Sample

In this example, a sample collection tube containing one or more markers is contained in a tamper-resistant sealed package, with a serial number on the package and the collection tube contained within the security pouch. A phlebotomist will draw a blood sample from the individual or animal to be tested and at least one witness will be required to sign a statement that the collection protocol has been followed. The phlebotomist will: 1) positively identify the individual, 2) open the sealed pouch and verify that the serial number on the pouch and collection tube matches, 3) collect the individual's blood sample using a butterfly needle provided with the kit and attaching the sample collection tube until filled, 4) remove the needle from the individual and remove the collection tube from the needle, 5) insert the needle into a tube containing a DNA destroying solution (described below) and attach an empty vacuum collection tube to the other end of the needle, so that the DNA destroying solution passes through the needle, 6) send the sample collection tube along with the rest of the used collection kit and chain of custody form to the forensic laboratory for analysis.

It is preferred to use a sealed vacuum tube as the collection device with the DNA and/or other markers contained within, so that the markers will not be able to get out into the environment. Alternatively, it is more preferred to add one or more markers to a collection matrix (preferably, FTA® paper manufactured by Fitzco) which binds fragments of DNA larger than 1000 base pairs.

The procedure may be videotaped to ensure compliance with the collection protocol. Another option may be to include a card with a photograph of the collection kit in its intact security pouch with a description of features of the security pouch, so that the individual to be tested could inspect the security pouch and sign his name to attest that the security pouch was intact and that the serial number on the security pouch and collection device were the same as those written on the chain of evidence custody form. The witness and phlebotomist will sign a chain of evidence custody form to attest that the security pouch was intact prior to the evidence collection, that the correct individual provided the sample, that the blood was drawn using the apparatus provided with the kit and put into the serial number marked blood collection tube or blood collection matrix provided with that specific kit, and that all ancillary collection devices were cleaned to destroy any residual blood. After the blood sample is collected, the butterfly needle with tubing (ancillary collection device, which could also be a needle and syringe) is removed from the individual and any remaining blood within the ancillary collection devices is destroyed by aspirating a DNA-destroying solution provided with the evidence collection kit (such as 10% bleach or hydrochloric acid at pH 2) through the ancillary collection device. Most likely, only a butterfly needle with its attached tubing would constitute the ancillary collection device. This butterfly needle could have a distinctive color so that it would be distinct from unmarked needles. After evidence collection, the used butterfly needle would be inserted into the DNA destroying solution and the other end of the butterfly would be inserted into a vacuum tube, which may contain an indicator substance, which changes color when the DNA destroying solution is added. The indicator reaction could also be modified so that the development of the final color would require the small amount of blood (iron) from the trace amount of residual blood contained in the butterfly needle. This colorimetric procedure would rapidly demonstrate to the witnesses that all blood that was not fully marked had been destroyed.

The ancillary collection devices may be coated on the interior surfaces with non-toxic markers, such as one or more chemicals which are easily detectable by mass spectroscopy. This will also ensure that no residual unmarked blood exists.

Example 2

Production of Marker Kit Having Nucleic Acid Markers

Nucleic acid markers will be produced by various means, which may include cloning, direct synthesis, PCR amplification and other means known in the art. Production of the markers will be performed at facilities physically separated from any testing laboratory, so that markers will not be inadvertently transferred to a forensic, clinical, paternity or veterinary test setting. Once produced, the individual nucleic acid markers from several different sources may be mixed into unique combinations. Other non-nucleic markers, such as proteins or easily identified chemicals can also be added to the marker combination. Each combination can be added to one or more sample collection or laboratory control devices, each bearing a unique serial number that will be associated with that unique combination of markers. Production of combinatorial mixtures may be easily performed by a robotic pipette station. All markers can be transferred using disposable pipettes with aerosol barrier filters to prevent cross contamination, or by single use syringes and needles. Information relating to the marker types and corresponding serial numbers can be stored in several formats, including optical CD and computer hard disk, with a backup copy maintained at a separate location. The markers may be added directly into a previously manufactured device by the use of a syringe and needle. In the case of a tube used as the collection or control device, the markers may be added to an empty tube, then freeze dried with vacuum centrifugation in the tube. Colored rubber stoppers can be placed on the tube while the tube is under vacuum. Unique colored stoppers may be used to readily distinguish the marked tubes.

In the case of a filter paper or blood collection matrix used as the collection or control device, solutions containing DNA and/or other markers can be placed onto the filter paper or blood collection matrix and dried. Blood spotted onto the filter paper or matrix would be marked due to the markers present on the device.

Marked butterfly needles can be produced by aspiration of a sterile solution of one or more non-toxic markers through the needle and tubing. The solution can then be allowed to dry in the butterfly needle, with or without vacuum or additional heat. Each needle can be given a serial number matched to a collection tube, and the one or more markers contained in the butterfly needle can be added to the data base for the tube. A blood sample should contain all the markers found in the butterfly needle and the collection tube. The tube and needle are then packaged together using aseptic technique in a security pouch, which is designed to be tamper resistant, and which may also be marked with the serial number of the collection device.

The devices according to the present invention can be made available to police departments, prisons, hospitals, forensic, clinical, paternity and veterinary laboratories, and other organizations involved in the collection of samples. The combination of markers present in the collection kit will not be disclosed to the organization which obtains the sample. This will help preserve the integrity of the sample taken from the individual.

If, in the case of forensic analysis, a suspect's blood was taken from the collection device and added to crime scene evidence, the full range of markers would be detectable in the crime scene evidence, thereby proving conclusively that the evidence had been contaminated. By using markers which are easy to detect by antibodies, mass spectroscopy, fluorescence, or other methods known to those of skill in the art, very small samples of evidence, such as blood spots, could be rapidly and inexpensively tested for the presence of markers. To ensure that the system according to the present invention is not defeated, it is preferred to use a nucleic acid markers or a combination of nucleic acid and non-nucleic acid markers, because certain non-nucleic acid markers may be removable by certain procedures used to purify the DNA contained in the evidence for forensic DNA analysis. Nucleic acid markers will co-purify with the evidentiary DNA, so they would be extremely difficult to remove.

If a laboratory was to attempt to manipulate evidence by amplifying the commonly used forensic DNA regions from the suspect, extensively purifying the products and then placing them on the evidence, this could be determined by further testing the evidence for less commonly used polymorphic regions. Those uncommonly tested regions from the suspect's genome would be absent, indicating evidence tampering.

Example 3

Testing for Presence or Absence of Markers

For non-nucleic acid marker a sample may be tested for the presence or absence of such markers by mass spectroscopy or by fluorescence, which could rapidly detect sample contamination. Markers such as nucleic acids which do not readily show up using instruments such as a mass spectrometer would be tested for as discussed below.

In the forensic setting, if either the defense or prosecution suspects that there has been evidence tampering or laboratory mixing of evidence and suspect samples, a sample of the unprocessed evidence or DNA extracted from the evidence may be sent to a certified forensic reference laboratory (certified by the manufacturer, FBI, NIST, or another agency). A sample from the suspect will not be necessary. This will eliminate the potential problem of cross-contamination at the reference laboratory. Upon notification, the manufacturer or an independent agency will provide the reference lab with a report of the markers that were contained in the collection device(s) used for the suspect or suspects in the case. The sequence of PCR primers to detect nucleic acid markers may be sent, or actual primers may be provided. If proteins were included in the collection device as markers, then detection antibodies may be provided, or a listing of suitable antibodies may be sent. The spectrums of non-nucleic acid marker chemicals will be included for all chemicals used, along with information on how best to detect them.

For each test done, the reference laboratory should run appropriate positive and negative controls. The absence of the markers in the evidence sample should be interpreted as ruling out contamination; whereas the presence of markers will implicate evidence mixing. If one or two of the DNA markers from the collection device are found in an evidentiary sample, it will be possible to test for the possibility of environmental presence of the DNA marker. This may be elucidated by the following example. Say a crime occurred in the penguin cage at a zoo, and a region of penguin DNA was used as one of the markers in the collection device used in that case. The penguin marker in the collection device will be a small defined region of penguin DNA. PCR or other DNA tests can be done with primers or probes for non-marker regions of the penguin genome, and if found, the positive result for penguin marker found in the evidence can be discounted. Specimen integrity can still be verified by the presence or absence of the other markers which were present in the collection device. By using DNA markers from a combination of rare, extinct and geographically isolated organisms, and artificially produced DNA, there would be little chance of all these sequences existing at any one crime scene, with the exception of the marker production facility.

The scope of the present invention is to be determined by the following claims.

I claim:

1. A device suitable for marking a collected sample, comprising:

collecting means for collecting the sample; and at least one detectable non-nucleic acid marker which is contained in at least a portion of the collecting means, wherein the at least one detectable non-nucleic acid marker is contactable with the sample upon collection of the sample to mark the collected sample upon contact of the sample with the at least a portion of the collecting means having the at least one detectable non-nucleic acid marker contained therein, and wherein the at least one detectable marker non-nucleic acid marker is other than a component which is already present in the sample and is inert to any component present in the sample; and wherein at least a portion of the detectable non-nucleic acid marker passes into all of a collected sample upon collection of the sample, and the non-nucleic acid marker marker is detectable in any portion of any sample that has been collected in the collecting means.

2. The device of claim 1, wherein the collecting means collects and contains the sample.

3. The device of claim 1, wherein the collecting means is selected from the group consisting of a tube and a membrane collection system.

4. The device of claim 1, wherein the collecting means is a tube and the at least one detectable non-nucleic acid marker is located on an interior surface of the tube.

5. The device of claim 1, wherein the collecting means is a membrane collection system and the at least one detectable non-nucleic acid marker is located on a surface of or is incorporated into the membrane collection system.

6. The device of claim 1, wherein the collecting means is a blood collection system.

7. The device of claim 1, wherein the sample is selected from the group consisting of a body fluid sample and a tissue sample.

8. The device of claim 1, wherein the sample is a human or animal sample.

9. The device of claim 1, wherein the at least one detectable non-nucleic acid marker comprises at least one member selected from the group consisting of a peptide, a protein, a fluorescent compound, an isotopic element, an isotopic compound, a stain and a dye.

10. The device of claim 1, further comprising identifying means for identifying at least one of the identify and the amount of the at least one detectable non-nucleic acid marker.

11. The device of claim 10, wherein the identifying means identifies at least one of the identity and the amount of the at least one detectable non-nucleic acid marker in code.

12. A kit suitable for marking a body fluid evidence sample, comprising:
   the device of claim 1;
   identifying means for identifying at least one of the identity and the amount of the at least one detectable marker; and
   tamper-evident sealing means for tamper-evident sealing of the collecting means and the at least one detectable marker.

13. The kit of claim 12, wherein the identifying means identifies at least one of the identity and the amount of the at least one detectable marker in code.

14. A method for marking a sample, comprising collecting the sample using a collection device having at least one detectable non-nucleic acid marker which is contained in at least a portion of the collecting device, wherein the at least one detectable non-nucleic acid marker is other than a component which is already present in the sample and is inert to any component present in the sample, and causing the sample to contact the at least one detectable non-nucleic acid marker to pass at least a portion of the at least one detectable non-nucleic acid marker into the sample to mark the sample; and wherein at least a portion of the detectable non-nucleic acid marker passes into all of a collected sample upon collection of the sample, and the non-nucleic acid marker is detectable in any portion of any sample that has been collected in the collecting means.

15. The method of claim 11, wherein the collection device further comprises identifying means for identifying in code at least one of the identity and the amount of the at least one detectable non-nucleic acid marker.

16. A method for determining the integrity of a marked sample, comprising:
   (a) providing a sample which is marked as recited in claim 15;
   (b) thereafter detecting at least one of an identity and an amount of the at least one detectable non-nucleic acid marker in the marked sample to provide a result; and
   (c) comparing the result from (b) with known information encoded in the identifying means as to at least one of the identity and the amount of the at least one detectable non-nucleic acid marker to determine the integrity of the marked sample.

17. A method for determining the integrity of a marked sample, comprising:
   (a) providing a sample which is marked as recited in claim 14;
   (b) thereafter detecting at least one of an identity and an amount of the at least one detectable non-nucleic acid marker in the marked sample to provide a result; and
   (c) comparing the result from (b) with known information as to at least one of the identity and the amount of the at least one detectable non-nucleic acid marker to determine the integrity of the marked sample.

18. A method of marking a human body fluid or tissue sample to confirm an identity of the sample at a later date, the method comprising:
   collecting the sample using a collection device having at least one detectable marker which is contained in at least a portion of the collecting device, wherein the at least one detectable marker is other than a component which is already present in the sample and is inert to any component present in the sample, and causing the sample to contact the at least one detectable marker to pass at least a portion of the at least one detectable marker into the sample to mark the sample,
   wherein the collection device comprises identifying means for identifying both of the identity and the amount of the at least one detectable marker so that one can confirm the identity of the second sample at a later date by comparing the at least one detectable marker in the sample and the identifying means; and wherein at least a portion of the detectable marker passes into all of a collected sample upon collection of the sample, and the marker is detectable in any portion of any sample that has been collected in the collecting means.

19. The method of claim 18, wherein the identifying means contains known information as to at least one of the identity and the amount of the at least one detectable marker encoded therein.

20. The method of claim 18 wherein the at least one detectable marker is a nucleic acid.

21. A method for determining that an unmarked first sample has not been contaminated by a marked second sample, the method comprising:
   collecting the second sample using a collection device having at least one detectable marker which is contained in at least a portion of the collecting device, wherein the at least one detectable marker is other than a component which is already present in the second sample and is inert to any component present in the second sample, and causing the second sample to contact the at least one detectable marker to pass at least a portion of the at least one detectable marker into the second sample to mark the second sample, wherein the collection device comprises identifying means for identifying at least one of the identity and the amount of the at least one detectable marker so that one can confirm the identity of the second sample of comparing the at least one detectable marker in the second sample and the identifying means; and wherein at least a portion of the detectable marker passes into all of a collected sample upon collection of the sample, and the marker is detectable in any portion of any sample that has been collected in the collecting means;

testing the first sample for the presence of the marker;

determining that the marker is not present in the first sample thereby indicating no contamination of the first sample by the second sample.

22. The method of claim 21 wherein the first sample and the second sample both comprise evidenciary human body fluid or tissue.

* * * * *